US009833317B2

United States Patent
Kaufmann

(10) Patent No.: US 9,833,317 B2
(45) Date of Patent: Dec. 5, 2017

(54) CATHETER DEVICE FOR MINIMALLY INVASIVE IMPLANTATION

(71) Applicant: BIOTRONIK AG, Buelach (CH)

(72) Inventor: Ralf Kaufmann, Loerrach (DE)

(73) Assignee: Biotronik AG, Buelach (CH)

( * ) Notice: Subject to any disclaimer, the term of this patent is extended or adjusted under 35 U.S.C. 154(b) by 365 days.

(21) Appl. No.: 14/621,866

(22) Filed: Feb. 13, 2015

(65) Prior Publication Data
US 2015/0272735 A1 Oct. 1, 2015

Related U.S. Application Data

(60) Provisional application No. 61/970,395, filed on Mar. 26, 2014.

(51) Int. Cl.
| | | |
|---|---|---|
| A61F 2/24 | (2006.01) |
| A61B 17/34 | (2006.01) |
| A61M 25/00 | (2006.01) |
| A61B 17/00 | (2006.01) |
| A61F 2/966 | (2013.01) |

(52) U.S. Cl.
CPC ...... *A61F 2/2436* (2013.01); *A61B 17/00234* (2013.01); *A61B 17/3417* (2013.01); *A61M 25/0043* (2013.01); *A61B 17/3415* (2013.01); *A61F 2/966* (2013.01); *A61F 2220/0025* (2013.01); *A61F 2230/008* (2013.01); *A61F 2230/0069* (2013.01); *A61F 2230/0078* (2013.01); *A61M 2025/0004* (2013.01); *A61M 2025/0062* (2013.01)

(58) Field of Classification Search
CPC ...... A61F 2/95; A61F 2002/011; A61F 2/966; A61F 2/2436; A61B 17/00234; A61B 17/3415; A61B 17/3417; A61B 2017/1205; A61B 2017/12054; A61M 2025/0004; A61M 2025/0062; A61M 25/0043; A61M 2025/0681
USPC ...... 623/1.11, 2.11; 606/108, 191, 194, 198, 606/200
See application file for complete search history.

(56) References Cited

U.S. PATENT DOCUMENTS

| | | | |
|---|---|---|---|
| 3,841,335 A | * | 10/1974 | Tarsitano ............. A61B 17/144 606/177 |
| 5,320,627 A | | 6/1994 | Sorensen et al. |
| 2003/0212411 A1 | | 11/2003 | Jansen et al. |
| 2004/0093061 A1 | | 5/2004 | Acosta et al. |
| 2005/0209670 A1 | | 9/2005 | George et al. |

(Continued)

FOREIGN PATENT DOCUMENTS

| | | |
|---|---|---|
| EP | 0747073 A1 | 12/1996 |
| EP | 1459706 B1 | 1/2004 |
| WO | 2010033698 A1 | 3/2010 |

OTHER PUBLICATIONS

European Search Report Dated Aug. 11, 2015.

*Primary Examiner* — Katherine M Shi
(74) *Attorney, Agent, or Firm* — Greer, Burns & Crain, Ltd.; Steven P. Fallon

(57) ABSTRACT

Catheter devices provide for rolling movement between the inner and outer catheter tubes with a roller assembly in a radial gap between the inner and outer catheter tubes. Devices of the invention are particularly useful in minimally invasive implantations, such as the implantation of a vascular implant. A particular application is interventional catheter-assisted aortic valve implantation.

16 Claims, 4 Drawing Sheets

(56) References Cited

U.S. PATENT DOCUMENTS

| | | |
|---|---|---|
| 2006/0041302 A1 | 2/2006 | Malewicz |
| 2006/0229574 A1 | 10/2006 | Sherman et al. |
| 2011/0213303 A1 | 9/2011 | Lentz et al. |
| 2012/0240694 A1* | 9/2012 | Isobe ..................... F16C 1/06 74/25 |
| 2013/0197552 A1* | 8/2013 | O'Brien, II ...... A61B 17/32002 606/170 |
| 2013/0204345 A1 | 8/2013 | Cully et al. |

* cited by examiner

CATHETER DEVICE FOR MINIMALLY INVASIVE IMPLANTATION

PRIORITY CLAIM

This application claims priority under 35 U.S.C. §119 from prior U.S. Provisional Application No. 61/970,395, filed Mar. 26, 2014.

FIELD OF THE INVENTION

A field of the invention is catheter devices.

BACKGROUND

Interventional catheter-assisted aortic valve implantation is a method for treating patients suffering from high-grade aortic valve stenosis. Here, similarly to a cardiac catheter examination, the implantation is performed via the artery in the groin (transfemorally), a small incision in the left-hand side of the chest above the apex of the heart (transapically) or via an upper partial sternotomy directly through the aorta (transaortally) of the patient. At the beating heart, the constricted, natural aortic valve is first expanded using a balloon (balloon valvuloplasty) and a vascular prosthesis with integrated biological heart valve is then introduced via a catheter and unfolds for implantation at the location of the diseased aortic valve.

In order to achieve this functionality, such a catheter device for aortic valve implantation typically has an outer catheter tube with a distal end and a proximal end and has an inner catheter tube guided therein at a radial distance in a manner displaceable relative thereto. Due to the relative movement of the two catheter tubes, a specific function of the catheter device can be implemented, such as the exposure of the balloon for expansion of the natural heart valve or the implantation of the actual valve prosthesis by release of the vascular prosthesis.

A typical conventional heart valve prosthesis consists basically of a main structure and a heart valve fastened and integrated therein. The heart valve itself may consist here of natural tissue (such as pericardium tissue from a pig or cow) or polymer tissue (Dacron or the like). Donor valves are also possible. The heart valve is fastened in the main structure, wherein it is usually sewn to the main structure. The main structure serves to anchor the vascular prosthesis at the location of the natural valve. The main structure is basically a stent and can be either self-expanding or expandable by a balloon. In the case of a catheter system of the type mentioned in the previous paragraph, the vascular prosthesis is covered by the outer catheter tube during the insertion and positioning at the site of implantation. The outer catheter tube is retracted for the implantation. In the case of a self-expanding main structure, the force that holds the main structure in its compressed state on the inner catheter tube is cancelled by retracting the catheter tube. The main structure thus expands and anchors at the location of the natural heart valve. In the case of a balloon-expandable main structure, this is exposed and can be expanded by retracting the outer catheter tube.

A problem with aortic valve implantation is caused by the catheter device being tightly curved in the aortic arch. This can create problematic friction between the outer and inner catheter tube. In particular, the increase in friction caused by the curvature can cause the catheter tubes to move stiffly relative to one another, and therefore the controllability of the catheter functions may be impaired.

The prior art discloses some solution approaches to this problem. It is known from US 2006/0229574 A1 in conjunction with catheter lumens sitting one inside the other to provide bumps and indentations on a surface that comes into contact with other catheter surfaces. The friction of such an undulating surface with a smooth surface lying thereagainst is reduced on the whole, and therefore a number of catheter tubes can move smoothly relative to one another.

EP 1 459 706 A1 discloses a method for applying a self-expanding stent to a catheter, where at least one of the involved components—that is to say the stent itself, corresponding mechanism for compression of the stent, the involved transfer tube or the catheter itself—is provided with a sliding coating consisting of a biocompatible lubricant in order to reduce the friction encountered with components movable relative to one another. A glycerol-containing lubricant is mentioned as a preferred example for such a lubricant.

It is known from EP 0 747 073 A1 to provide the outer surface of the inner catheter tube of a medical catheter device and the inner surfaces of the outer catheter tube thereof with a fluid layer in order to overcome the problems concerning friction from the inner catheter tube to the outer catheter tube in the event of a relative movement. In this context, the use of materials having a low coefficient of friction, such as PTFE, or the application of a lubricant, for example in the form of a hydrogel, is mentioned as being known. In addition, this document teaches the application of a permanent fluid layer in the form of a heparin-containing hydrogel.

A delivery system for a self-expanding artificial heart valve with use of a rolling membrane is presented in WO 2010/033698 A1. Here, the friction between the catheter sleeve and the heart valve to be implanted is considerably reduced by the process of rolling the rolling membrane over mechanical paths. Such a rolling membrane can only be used, however, at the end of a catheter device.

US 2011/0213303 A1 discloses a catheter that causes what is known as a "goose bump"—like surface structure for drastic reduction of the friction of the surface formed in this way. The "goose bump" structure is produced by use of a thermoplastic material in the form of polyamide and an elastomer, such as a polyester block amide, in which microscopic particles, such as glass beads, are embedded at the surface. The friction coefficient that can be achieved as a result is compared with that of PTFE.

SUMMARY OF THE INVENTION

A preferred catheter device of the invention provides for minimally invasive implantation. The catheter device includes an outer catheter tube having a distal end and a proximal end. An inner catheter tube is guided within the outer catheter tube at a radial distance and is displaceable relative to the outer catheter tube. A roller assembly is disposed in the radial gap between the inner and outer catheter tube. The roller assembly includes roller structures distributed over one or more delimited length portions of the catheter device. The outer catheter tube is supported in a rolling relationship via its inner face on the rolling structures and the inner catheter tube is supported in a rolling relationship via its outer face on the roller structures

DESCRIPTION OF THE DRAWINGS

Further features, details and advantages of the invention will emerge from the following description of an exemplary embodiment with reference to the accompanying drawings, in which.

DETAILED DESCRIPTION OF THE PREFERRED EMBODIMENTS

Figure 1:
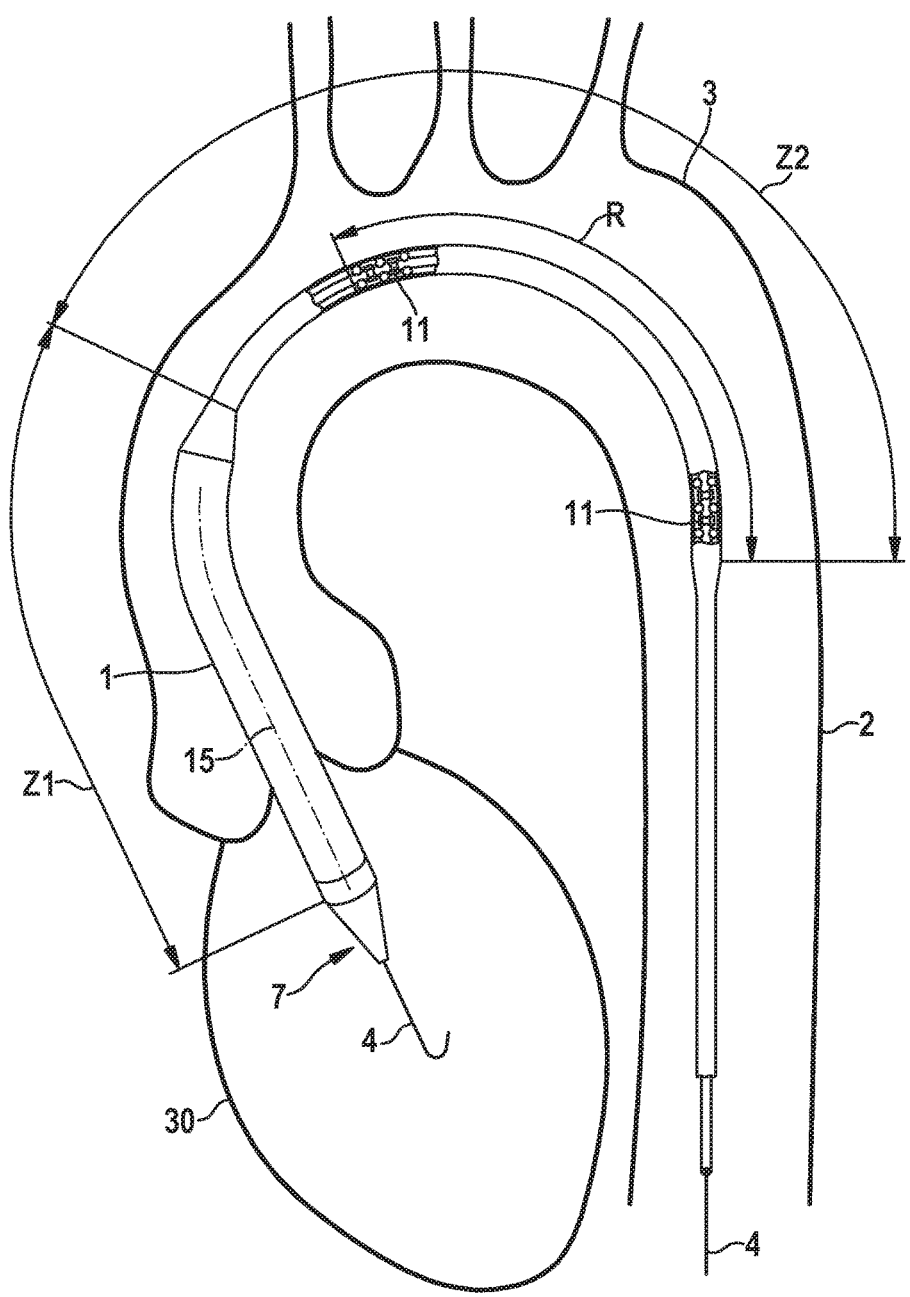
FIG. 1 shows a schematic perspective view of a catheter device in the implanted state.

Catheter devices of the invention provide for rolling movement between the inner and outer catheter tubes with a roller assembly in a radial gap between the inner and outer catheter tubes. Devices of the invention are particularly useful in minimally invasive implantations, such as the implantation of a vascular implant. A particular application is interventional catheter-assisted aortic valve implantation. The present invention is described primarily on the basis of the example of implantation of an aortic valve, however it is not limited to this application. The present invention is suitable for any catheter device in which an outer catheter tube is moved axially with respect to an inner catheter tube. Another example application is a catheter device for releasing a self-expanding stent.

Embodiments of the invention provide a catheter device for the minimally invasive implantation of a vascular implant having an outer catheter tube and an inner catheter tube guided therein at a radial distance in a manner displaceable relative thereto, such that the friction between the two tubes is as low as possible without use of surface structures or surface coatings of the adjacent surfaces.

Embodiments of the invention provide a catheter device with a roller assembly that is provided in the radial gap between the inner and outer catheter tube. This roller assembly has roller structures distributed over one or more delimited length portions, the outer catheter tube being supported in a rolling manner via its inner face on the roller structures and the inner catheter tube being supported in a rolling manner via its outer face on the roller structures.

Preferred catheter devices can advantageously be formed from conventional catheter tubes, while friction is minimized by mechanical through the roller assembly. There is thus no need for any coatings, which potentially cause side effects, or for complex surface structures.

With the aid of the relative displaceability of reduced friction between the outer and inner catheter tube, the vascular implant can be released more accurately.

In accordance with a preferred embodiment, the roller structures are barbell-shaped and are oriented with their rolling axis transverse to the longitudinal direction of the catheter. Here, the periphery of the weight-plate-shaped roller portions arranged at the end form the rolling surface for the outer catheter tube. The connection region between the weight-plate-shaped roller portions serves as a rolling surface for the inner catheter tube. Due to this barbell-shaped embodiment, a functional separation of different zones of the roller structures is thus achieved, such that these can each be adapted optimally to their intended use. Within the scope of the application a barbell-shaped structure is understood to be as structure having an axis of rotation at both ends of which a rotationally symmetrical element, such as a plate, is arranged.

In another preferred embodiment of the invention, the roller structures are formed in the manner of a diabolo. Within the scope of the application a diabolo is a geometric figure which is composed of two cones or truncated cones or of two hemispheres or hemisphere shells. Here, the cones or truncated cones are interconnected on the pointed side. The two hemispheres or hemisphere shells are interconnected in such a way that the sectional area of the sphere or the openings of the hemispherical shells point outwardly. A rotational structure that is rotationally symmetrical with respect to the connecting axis of the cones or hemispheres is thus created. The diabolo-shaped roller structures are expediently dimensioned and oriented here similarly to the barbell-shaped roller structures.

For example, the rolling surface of the roller structures for the inner catheter tube may thus be grooved in accordance with the outer diameter of the inner catheter tube, such that the inner catheter tube is guided particularly precisely between the roller structures.

In a further preferred embodiment of the invention, the inner face of the outer catheter has a polygonal cross section. The polygonal cross section is expediently adapted here to the dimension and number of roller structures per cross section. If, for example, three roller structures are arranged in a given cross section of the catheter, the inner face of the outer catheter expediently has a cross section in the shape of a regular hexagon. For example, barbell-shaped or diabolo-shaped roller structures are thus arranged on three sides of the hexagon and move in a guided manner over the outer face of the inner tube in the event of a corresponding relative movement between the outer tube and inner tube.

An embodiment of the roller structure in the form of spheres or cylinders is an alternate embodiment, this embodiment being of simple design and also easy to produce.

The distribution of the roller structures within the catheter device can be optimized in a preferred embodiment, for example by distributing a group of roller structures in the peripheral direction of the radial gap within a length portion of the catheter device. A cleaner guidance of the two catheter tubes relative to one another is thus achieved in this length portion. The positioning of the length portions can be adapted here in each case to the intended use of the catheter device. In accordance with a preferred embodiment of the catheter device, the roller assembly with one or more length portions is arranged in particular only in the longitudinal region of the catheter device that comes to rest in the aortic arch during aortic valve implantation. The catheter is thus adapted optimally to this intended use.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIG. 1 shows a catheter device 1 for interventional catheter-assisted aortic valve implantation, wherein the catheter device 1 in the aorta 2 is illustrated with the tip in the right ventricle of the heart 30 of a patient. Here, the catheter device 1 has the tightest curvature in the region of the aortic arch 3. To position the catheter device 1, a guide wire 4 is provided, on which the catheter device 1 can then be slid via a corresponding lumen 5 in the inner catheter tube 6 into the position shown in FIG. 1. A valve prosthesis (not illustrated) is mounted on the distal end 7 of the catheter device 1 and is placed at the location of the diseased aortic valve once this has been expanded by means of a balloon. The valve prosthesis takes up the portion Z1 of the catheter device 1 and is covered in FIG. 1 by the outer catheter tube.

The proximal end of the catheter device 1 is not illustrated in FIG. 1.

Figure 2:
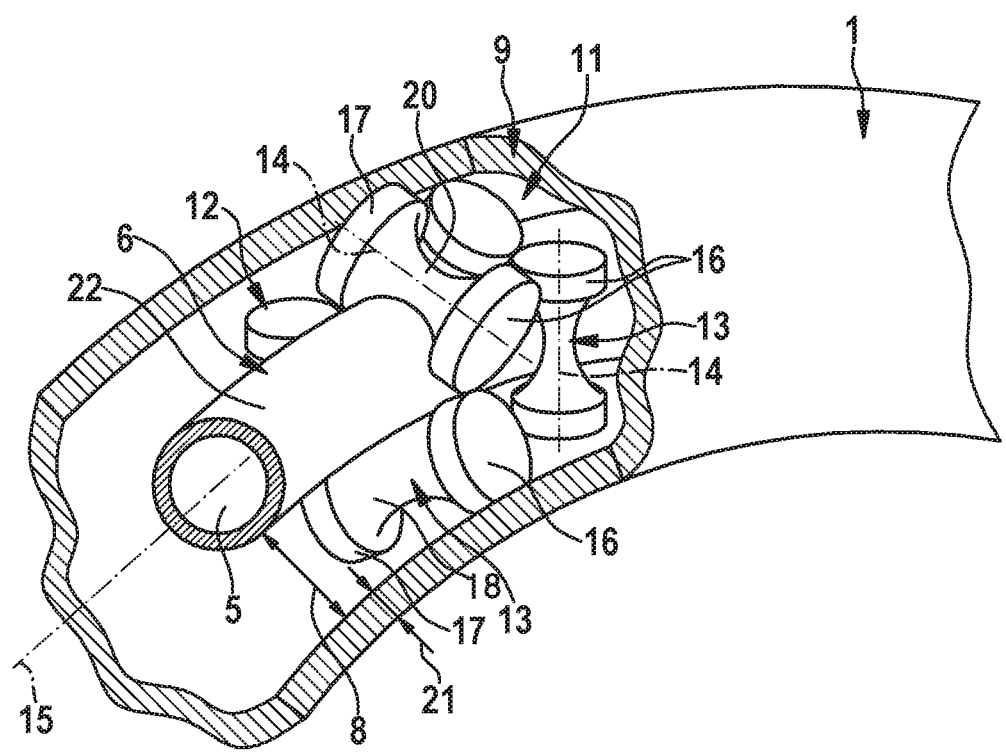
FIG. 2 shows a partly cut-away detail of the catheter device in a perspective view.

As is clear from FIG. 2, an outer catheter tube 9 is positioned on the aforementioned inner catheter tube 6 with radial spacing 8 separating the outer catheter tube 9 from the inner catheter tube 6. The inner and outer catheter tube 6, 9 are displaceable relative to one another.

In order to ensure a displaceability of the two catheter tubes 6, 9 with as little friction as possible, in particular in the region of the aortic arch 3 with the large curvature of the catheter device 1, the catheter device 1, for example in each length portion R indicated in FIG. 1, has a roller assembly 11 (visible in FIG. 2) in the radial gap 8, the roller assembly being formed in each case from a plurality of roller structures 13. The latter are each preferably formed in a barbell-shaped manner and are oriented with their rolling axis 14 transverse to the longitudinal axis 15 of the catheter. The periphery of the weight-plate-shaped roller portions 16, arranged at the end, of the roller structures 13 form the rolling surface 17, by means of which they are supported in a rolling manner on the inner face 21 of the outer catheter tube 9. The inner face of the outer catheter tube 9 has a hexagonal cross section in this embodiment, wherein the side lengths of the hexagon correspond to the length of the barbell-shaped roller structures 13. The connecting region 18 between the weight-plate-shaped rolling portions 16 is grooved in accordance with the outer diameter 19 of the inner catheter tube 6, such that the inner catheter tube 6 is nestled via its outer face 22 in this connecting region 18, which forms the rolling surface 20 for the inner catheter tube, and the inner catheter tube 6 can be guided cleanly relative to the outer catheter tube 9. Since the roller structures 13 are each distributed in groups in the length portions R in the peripheral direction of the radial gap 8, the friction-reducing effect of the roller assemblies 11 is isotropic, that is to say independent of the direction of curvature of the catheter device 1.

Figure 3:
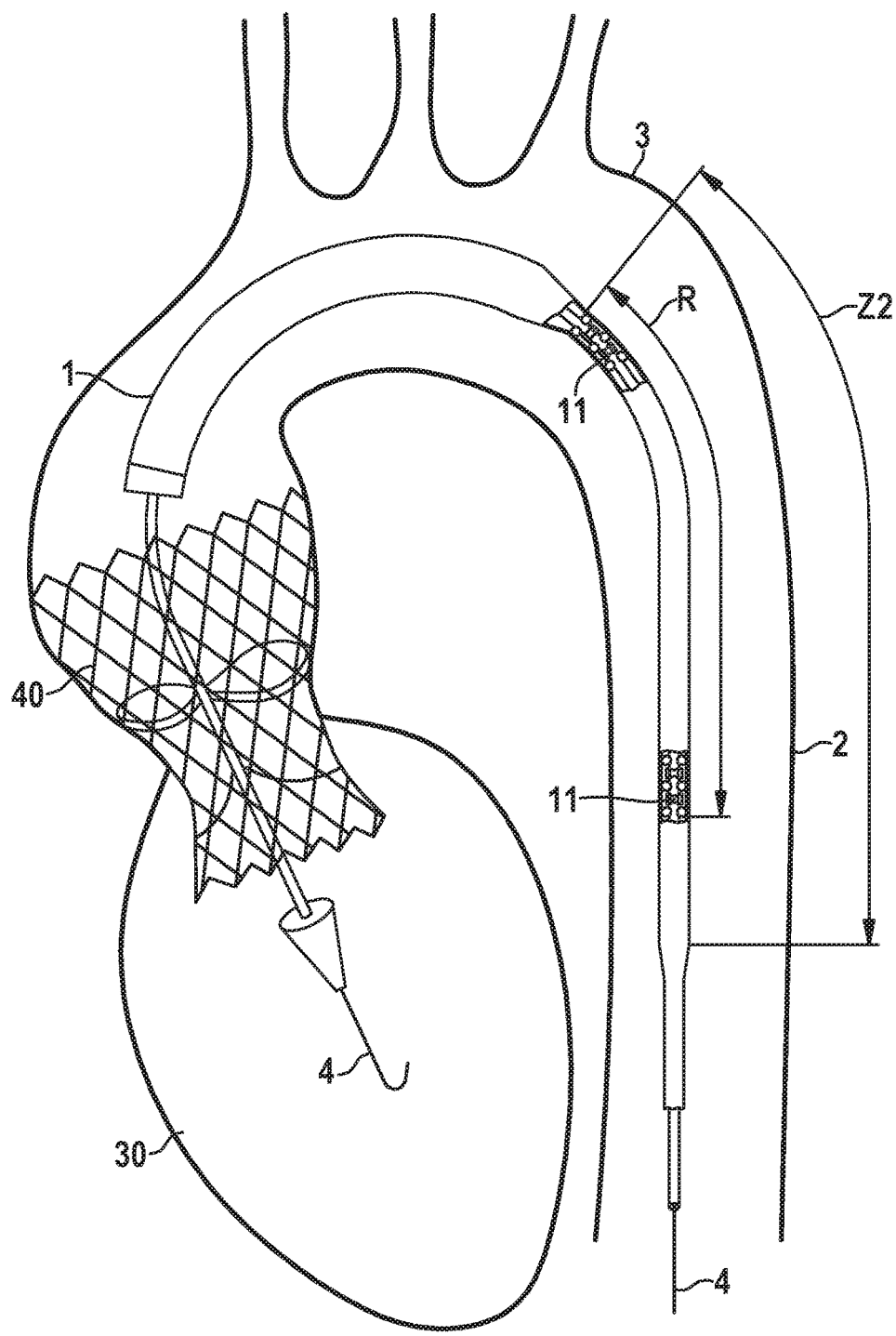
FIG. 3 shows a schematic perspective view of a catheter device after implantation of the heart valve prosthesis.

FIG. 3 shows the catheter device 1 after implantation of the heart valve prosthesis 40 in the annulus of the heart 30. Accordingly, the outer catheter tube 9 is retracted here practically completely and the two zones R and Z2 are displaced proximally. When retracting the outer catheter tube 9, the roller structures 13 perform a rolling movement, as already discussed. Here, the inner parts of the roller structures 13 roll via their rolling surface 20 over the inner catheter tube 6, whereas the outer plate-shaped portions 16 roll via their rolling surface 17 over the outer catheter tube 9. Due to the different diameter, the zone Z2 of the outer catheter tube 9 is displaced back proximally further than the rolling zone R accordingly.

Figure 4A:
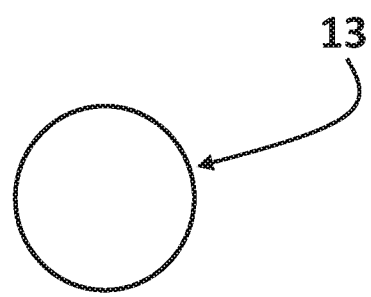
FIGS. 4A&4B show schematic view of alternate roller structures for the catheter device.
Figure 4B:
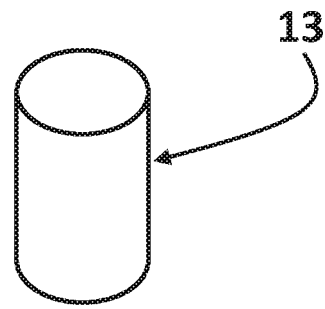

FIGS. 4A and 4B show alternative roller structures 13 respectively in the form of a spherical and cylindrical roller structure.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A catheter device for minimally invasive implantation of a vascular implant, comprising an outer catheter tube having a distal end and a proximal end, the outer catheter tube being sized and configured for vascular insertion, an inner catheter tube guided within the outer catheter tube at a radial distance and axially displaceable relative to the outer catheter, a vascular implant mounted on a distal end of the inner catheter tube and covered by the outer catheter tube until the outer catheter tube is retracted;

a roller assembly in a radial gap between the inner and outer catheter tube, said roller assembly having roller structures distributed over one or more delimited length portions of the catheter device, the outer catheter tube being supported in a rolling relationship via its inner face on said roller structures and the inner catheter tube being supported in a rolling relationship via its outer face on said roller structures.

2. The catheter device as claimed in claim 1, wherein the roller structures comprise spherical or cylindrical roller structures.

3. The catheter device as claimed in claim 1, wherein a group of roller structures is distributed in the peripheral direction of the radial gap within a length portion of the catheter device.

4. The catheter device as claimed in claim 1 for interventional catheter-assisted aortic valve implantation, wherein the roller assembly is arranged only in the longitudinal region of the catheter device that comes to rest in the aortic arch during aortic valve implantation.

5. The catheter device as claimed in claim 1, wherein the vascular implant comprises a heart valve prosthesis.

6. The catheter device as claimed in claim 1, wherein the vascular implant comprises a self-expanding stent.

7. The catheter device as claimed in claim 1, wherein the roller structures are barbell-shaped and are oriented with their rolling axis transverse to the longitudinal axis of the catheter.

8. The catheter device as claimed in claim 1, wherein the roller structures are diabolo-shaped and are oriented with their rolling axis transverse to the longitudinal axis of the catheter.

9. A catheter device for minimally invasive implantation, comprising an outer catheter tube having a distal end and a proximal end, an inner catheter tube guided within the outer catheter tube at a radial distance and displaceable relative to the outer catheter, a roller assembly in a radial gap between the inner and outer catheter tube, said roller assembly having roller structures distributed over one or more delimited length portions of the catheter device, the outer catheter tube being supported in a rolling relationship via its inner face on said roller structures and the inner catheter tube being supported in a rolling relationship via its outer face on said roller structures, wherein the roller structures are barbell-shaped or diabolo-shaped and are oriented with their rolling axis transverse to the longitudinal axis of the catheter.

10. The catheter device as claimed in claim 9, wherein said roller structures comprise weight-plate-shaped roller portions with a periphery forming a rolling surface for the outer catheter tube and a connection region between the weight-plate-shaped roller portions forming a rolling surface for the inner catheter tube.

11. The catheter device as claimed in claim 10, wherein the rolling surface for the inner catheter tube is grooved in accordance with the outer diameter of the inner catheter tube.

12. The catheter device as claimed in claim 9, wherein the inner face of the outer catheter tube comprises a polygonal cross section.

13. The catheter device as claimed in claim 12, wherein the polygonal cross section comprises a hexagonal cross section.

14. The catheter device as claimed in claim 9, further comprising a vascular implant mounted on a distal end of the inner catheter tube and covered by the outer catheter tube until the outer catheter tube is retracted.

15. The catheter device as claimed in claim 14, wherein the vascular implant comprises a heart valve prosthesis.

16. The catheter device as claimed in claim 14, wherein the vascular implant comprises a self-expanding stent.

\* \* \* \* \*